United States Patent [19]

Hamlin

[11] Patent Number: 4,780,565
[45] Date of Patent: Oct. 25, 1988

[54] PRODUCTION OF ALKYLENE GLYCOL ETHER CARBOXYLATES

[75] Inventor: John E. Hamlin, Hull, England

[73] Assignee: BP Chemicals Limited, London, England

[21] Appl. No.: 21,695

[22] Filed: Mar. 4, 1987

[30] Foreign Application Priority Data

Mar. 8, 1986 [GB] United Kingdom ................ 8605753

[51] Int. Cl.[4] ...................... C07C 67/26; C07C 67/36
[52] U.S. Cl. ..................................... 560/240; 560/93; 560/112; 560/199; 560/209; 560/200
[58] Field of Search .............. 560/240, 200, 199, 209, 560/112, 93, 263

[56] References Cited

U.S. PATENT DOCUMENTS 4,069,242  1/1978  Gurgiolo .......................... 560/240 X
4,665,236  5/1987  Edwards .......................... 560/240 X

FOREIGN PATENT DOCUMENTS 3008174  9/1981  Fed. Rep. of Germany ...... 560/240
44-9365   4/1969  Japan ................................. 560/240
1204987   9/1970  United Kingdom ............... 560/240

Primary Examiner—Vivian Garner
Attorney, Agent, or Firm—Brooks Haidt Haffner & Delahunty

[57] ABSTRACT

Alkylene glycol ether carboxylates are produced by reacting at elevated temperature an alkylene oxide and a carboxylate ester in the presence as catalyst of a [bis(-trihydrocarbylphosphine)iminium]$_2$MO$_4$ compound wherein M is either molybdenum or tungsten.

8 Claims, No Drawings

PRODUCTION OF ALKYLENE GLYCOL ETHER CARBOXYLATES

The present invention relates to a process for the production an alkylene glycol ether carboxylate by the reaction of an alkylene oxide and a carboxylate ester, for example the production of methoxypropylacetate by the reaction of propylene oxide and methyl acetate.

Methoxypropylacetate is an important solvent in, for example, paints and inks. It is currently manufactured by the esterification of methoxypropanol (derived from the reaction of propylene oxide and methanol) with acetic acid using, as catalyst, p-toluenesulphonic acid. In effect this represents a two-step reaction. It would be desirable to produce methoxypropylacetate in a single step.

It is known to produce alkylene glycol ether carboxylates by reacting an alkylene oxide with a carboxylate ester. Thus, German Offen. No. 2,951,080 describes the use of a zirconium halide catalyst and a cocatalyst from the group consisting of benzotriazole, N-alkylamides, N-($C_{1-4}$-alkyl) pyrrolidone, or primary, secondary or tertiary amines in this reaction. Japanese Kokai Tokkyo Koho No. 81 36,431 describes the production of alkylene glycol ether acetates by reacting alkylene oxides with alkyl acetates over calcined hydrotalcite catalysts.

In our experience the use of prior art catalysts is accompanied by disadvantages associated with selectivity and/or catalyst lifetime.

We have now found that the use of certain compounds of molybdenum and tungsten, for example $(PPN)_2MoO_4$, wherein PPN represents bis(triphenylphosphine)iminium, as catalysts in the production of an alkylene glycol ether carboxylate by the reaction of an alkylene oxide and a carboxylate ester can provide improved selectivity to the desired product.

Accordingly, the present invention provides a process for the production of an alkylene glycol ether carboxylate which process comprises reacting at elevated temperature an alkylene oxide and a carboxylate ester in the presence as catalyst of a [bis(trihydrocarbylphosphine)iminium]$_2$MoO$_4$ compound (I) wherein M is either molybdenum or tungsten.

As the alkylene oxide there may be used for example ethylene oxide, propylene oxide or a butylene oxide.

As the carboxylate ester there may suitably be used an ester of the formula RCOOR$^1$ wherein R is either hydrogen or a hydrocarbyl group and R$^1$ is a hydrocarbyl group. Suitably the hydrocarbyl groups may be alkyl groups, for example a $C_1$–$C_4$ alkyl group.

In a preferred reaction propylene oxide is reacted with methyl acetate to produce methoxypropylacetate.

In another preferred reaction propylene oxide is reacted with ethyl acetate to produce ethoxypropylacetate.

The catalyst is a [bis(trihydrocarbylphosphine)iminium]$_2$MoO$_4$ compound, wherein M is either molybdenum or tungsten, preferably molybdenum. The hydrocarbyl group may suitably be either alkyl or aryl or a substituted derivative thereof. Preferably the hydrocarbyl group is phenyl. A preferred catalyst is [bis(triphenylphosphine)iminium]$_2$MoO$_4$, hereinafter referred to as $(PPN)_2MoO_4$. The aforesaid compounds may suitably be prepared by reacting an alkali metal molybdate or tungstate, for example sodium molybdate, with a trihydrocarbylphosphine iminium halide, for example triphenylphosphine iminium chloride in aqueous media thereby to precipitate the [bis(trihydrocarbylphosphine)iminium]$_2$MoO$_4$ compound, and thereafter recovering the precipitate from the aqueous media. Thereafter, the precipitate may be washed, suitably with water and dried.

In addition to the catalyst, it is preferred to add a promoter. Suitable promoters include trihydrocarbyl phosphines, wherein the hydrocarbyl group is an aliphatic group, such as for example an alkyl group, or an aryl group such as a phenyl group. A preferred promoter is triphenylphosphine. An advantage of using a promoter is that the selectivity to the alkylene glycol ether carboxylate may be substantially increased.

The process is preferably operated in the absence of a solvent, other than the reactants. It has been found that the use of solvents such as acetone or dichloromethane can lead to lower selectivities to methoxypropylacetate by reason of increased by-product formation.

The reaction of an alkylene oxide with methyl acetate, for example, produces both the methoxypropyl-2-acetate and the methoxypropyl-1-acetate isomers in a similar ratio (about 9:1) to that observed in the conventional reaction of methoxypropanol with acetic acid.

The process of the invention may suitably be operated at elevated temperatures, typically in the range from 50° to 250° C. Conveniently atmospheric pressure may be employed, though both subatmospheric and superatmospheric pressure may be employed if desired.

The process may be operated batchwise or continuously, preferably continuously.

The desired alkylene glycol ether carboxylate may be recovered from the reaction product by conventional methods.

The invention will now be further illustrated by reference to the following Examples.

EXAMPLE 1

Methyl acetate (0.4 g; 5.4 mmol) and propylene oxide (0.4 g; 7 mmol) were charged into a 1.6 ml microreactor together with $(PPN)_2MoO_4$ (0.05 g; 0.04 mmol). The microreactor was sealed and plunged into an oil bath maintained at 187° C. After 1 hour the microreactor was removed from the oil bath and cooled to room temperature. The contents were then removed and analysed by GC.

EXAMPLE 2

Example 1 was repeated except that triphenylphosphine (0.1 g; 0.4 mmol) was added to the reaction mixture in the microreactor.

EXAMPLE 3

Example 1 was repeated except that dichloromethane (0.4 ml) was added as solvent.

EXAMPLE 4

Example 1 was repeated except that acetone (0.4 ml) was added as solvent.

EXAMPLE 5

The procedure of Example 2 was repeated except that ethyl acetate (0.52 g; 5.9 mmol) was used in place of methyl acetate and the amount of propylene oxide was 0.35 g (6.0 mmol).

The conversion of propylene oxide was 99% and the product selectivities (%) were:
  ethoxypropylacetate—35
  ethoxypropanol—8 high boilers—54
others—3

COMPARISON TEST 1

Example 2 was repeated except that $ZrCl_4$ was used as catalyst and a promoter in the form of N-methyl pyrrolidone was added.

The results of Examples 1 to 4 and Comparison Test 1 are given in the accompanying Table.

COMPARISON TEST 2

Example 1 was repeated except that instead of the $(PPN)_2MoO_4$ catalyst there was added PPN chloride.
No significant catalytic activity was observed.

COMPARISON TEST 3

Example 2 was repeated except that $(PPN)_2MoO_4$ was omitted.
No significant catalytic activity was observed.

TABLE

| | | Reaction of Propylene Oxide (PO) with Methyl Acetate | | | | | |
|---|---|---|---|---|---|---|---|
| | | Conversion of PO (%) | Product Selectivities (%) | | | | |
| Example | Catalyst | | MPA | MP | DMD | MPO | high boilers | others |
| 1 | $(PPN)_2MoO_4$ | 96 | 21.4 | 10.3 | 0.5 | 0.5 | 66.5 | 0.8 |
| 2 | $(PPN)_2MoO_4$; $PPh_3$ | 99 | 29.4 | 5.9 | 0.2 | 0.5 | 62.4 | 1.6 |
| 3 | $(PPN)_2MoO_4$; $CH_2Cl_2$ | 97 | 7.6 | 4.7 | 3.1 | 1.7 | 81.8 | 1.1 |
| 4 | $(PPN)_2MoO_4$; acetone | 95 | 8.5 | 13.8 | 1.1 | 17.7 | 58.9 | — |
| CT 1 | $ZrCl_4$; N—methyl pyrrolidone | 98 | 18.8 | 9.3 | 0.8 | 0.4 | 69.9 | 0.8 |

In the above Table:
MPA = methoxypropylacetate
MP = methoxypropanol
DMD = 2,5-dimethyl-1,4-dioxane
MPO = methylpentenone In the aforesaid Examples 1 to 4 at least 25% of the reaction product was unreacted methyl acetate.

With reference to the Table, it can be seen that the use of dichloromethane (Example 3) and acetone (Example 4) as solvents lowers the selectivity to MPA by comparison with Example 1 in which no solvent was used. Similar conversions but higher selectivities to MPA are obtained with catalysts according to the invention (Examples 1 and 2) than are obtained with a prior art catalyst (Comparison Test 1).

I claim:

1. A process for the production of an alkylene glycol ether carboxylate which process comprises reacting at an elevated temperature of from 50° to 250° C. an alkylene oxide selected from ethylene oxide, propylene oxide and butylene oxide, and a carboxylate ester in the presence as catalyst of a [bis(trihydrocarbylphosphine)iminium]$_2$MO$_4$ compound (I) and optionally, in the presence of a trihydrocarbyl phosphine as a promoter, wherein M is either molybdenum or tungsten; and the carboxylate ester is an ester of the formula $RCOOR^1$ wherein R is either hydrogen or a $C_1$ to $C_4$ alkyl group and $R^1$ is a $C_1$ to $C_4$ alkyl group.

2. A process according to claim 1 wherein the hydrocarbyl group of the compound (I) is either alkyl or aryl.

3. A process according to claim 2 wherein the hydrocarbyl group is phenyl.

4. A process according to claim 1 wherein M in the compound (I) is molybdenum.

5. A process according to claim 1 wherein a promoter which is a trihydrocarbyl phosphine is employed.

6. A process according to claim 5 wherein the promoter is triphenylphosphine.

7. A process according to claim 1 wherein no solvent other than the reactants is employed.

8. A process according to claim 1 wherein propylene oxide is reacted with either methyl acetate to produce methoxypropylacetate or with ethyl acetate to produce ethoxypropylacetate.

* * * * *